United States Patent
Karst et al.

(10) Patent No.: US 9,414,769 B2
(45) Date of Patent: Aug. 16, 2016

(54) METHOD FOR DETERMINING HEMODYNAMIC EFFECTS

(71) Applicant: Covidien LP, Boulder, CO (US)

(72) Inventors: Edward Karst, South Pasadena, CA (US); Joseph Douglas Vandine, Newark, CA (US); Charles E. Porges, Orinda, CA (US); Clark R. Baker, Jr., Newman, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 13/971,478

(22) Filed: Aug. 20, 2013

(65) Prior Publication Data

US 2013/0338514 A1    Dec. 19, 2013

Related U.S. Application Data

(63) Continuation of application No. 12/561,960, filed on Sep. 17, 2009, now Pat. No. 8,551,006.

(60) Provisional application No. 61/097,763, filed on Sep. 17, 2008.

(51) Int. Cl.
*A61B 5/08* (2006.01)
*A61B 5/029* (2006.01)
(Continued)

(52) U.S. Cl.
CPC .............. *A61B 5/0806* (2013.01); *A61B 5/0205* (2013.01); *A61B 5/029* (2013.01); *A61B 5/14551* (2013.01); *A61B 5/4035* (2013.01)

(58) Field of Classification Search
CPC .... A61B 5/0806; A61B 5/0205; A61B 5/029; A61B 5/14551; A61B 5/022; A61B 5/026
USPC ........................... 600/507, 504, 481, 483, 484
See application file for complete search history.

(56) References Cited

U.S. PATENT DOCUMENTS 3,805,780 A   4/1974 Cramer et al.
3,941,124 A   3/1976 Rodewald et al.
(Continued)

FOREIGN PATENT DOCUMENTS

WO   WO 2004000114   12/2003
WO   WO 2007085110   8/2007
WO   WO 2007145948   12/2007

OTHER PUBLICATIONS

Reuter et al., Stroke vol. variation for assessment of cardiac responsiveness to volume loading in mechanically ventilated patients after cardiac surgery, Intensive Care Med, vol. 28, 2002, pp. 392-398.*

(Continued)

*Primary Examiner* — Michael Kahelin
*Assistant Examiner* — Tho Tran

(57) ABSTRACT

The present disclosure relates, in some embodiments, to devices, systems, and/or methods for collecting, processing, and/or displaying stroke volume and/or cardiac output data. For example, a device for assessing changes in cardiac output and/or stroke volume of a subject receiving airway support may comprise a processor; an airway sensor in communication with the processor, wherein the airway sensor is configured and arranged to sense pressure in the subject's airway, lungs, and/or intrapleural space over time; a blood volume sensor in communication with the processor, wherein the blood volume sensor is configured and arranged to sense pulsatile volume of blood in a tissue of the subject over time; and a display configured and arranged to display a representative of an airway pressure, a pulsatile blood volume, a photoplethysmogram, a photoplethysmogram ratio, the determined cardiac output and/or stroke volume, or combinations thereof. A method of assessing changes in cardiac output or stroke volume of a subject receiving airway support from a breathing assistance system may comprise sensing pressure in the subject's airway as a function of time, sensing pulsatile volume of blood in a tissue of the subject as a function of time, producing a photoplethysmogram from the sensed pulsatile volume, determining the ratio of the amplitude of the photoplethysmogram during inhalation to the amplitude of the photoplethysmogram during exhalation, and determining the change in cardiac output or stroke volume of the subject using the determined ratio.

20 Claims, 2 Drawing Sheets

(51) Int. Cl.
*A61B 5/1455* (2006.01)
*A61B 5/0205* (2006.01)
*A61B 5/00* (2006.01)

(56) References Cited

U.S. PATENT DOCUMENTS

| | | | |
|---|---|---|---|
| 4,056,098 A | 11/1977 | Michel et al. | |
| 4,305,388 A | 12/1981 | Brisson | |
| 4,340,044 A | 7/1982 | Levy et al. | |
| 4,752,089 A | 6/1988 | Carter | |
| 4,921,642 A | 5/1990 | LaTorraca | |
| 4,939,647 A | 7/1990 | Clough et al. | |
| 4,954,799 A | 9/1990 | Kumar | |
| 4,971,052 A | 11/1990 | Edwards | |
| 4,986,268 A | 1/1991 | Tehrani | |
| 5,057,822 A | 10/1991 | Hoffman | |
| 5,072,737 A | 12/1991 | Goulding | |
| 5,094,235 A | 3/1992 | Westenskow et al. | |
| 5,150,291 A | 9/1992 | Cummings et al. | |
| 5,161,525 A | 11/1992 | Kimm et al. | |
| 5,178,151 A * | 1/1993 | Sackner | 600/485 |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,315,989 A | 5/1994 | Tobia | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,357,946 A | 10/1994 | Kee et al. | |
| 5,365,922 A | 11/1994 | Raemer | |
| 5,368,019 A | 11/1994 | LaTorraca | |
| 5,383,449 A | 1/1995 | Forare et al. | |
| 5,385,142 A | 1/1995 | Brady et al. | |
| 5,388,575 A | 2/1995 | Taube | |
| 5,390,666 A | 2/1995 | Kimm et al. | |
| 5,398,682 A | 3/1995 | Lynn | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,429,123 A | 7/1995 | Shaffer et al. | |
| 5,438,980 A | 8/1995 | Phillips | |
| 5,443,075 A | 8/1995 | Holscher | |
| 5,503,147 A | 4/1996 | Bertheau | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,535,738 A | 7/1996 | Estes et al. | |
| 5,540,220 A | 7/1996 | Gropper et al. | |
| 5,542,415 A | 8/1996 | Brody | |
| 5,544,674 A | 8/1996 | Kelly | |
| 5,549,106 A | 8/1996 | Gruenke et al. | |
| 5,551,419 A | 9/1996 | Froehlich et al. | |
| 5,596,984 A | 1/1997 | O'Mahoney et al. | |
| 5,605,151 A | 2/1997 | Lynn | |
| 5,623,923 A | 4/1997 | Bertheau et al. | |
| 5,630,411 A | 5/1997 | Holscher | |
| 5,632,270 A | 5/1997 | O'Mahoney et al. | |
| 5,645,048 A | 7/1997 | Brodsky et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,692,497 A | 12/1997 | Schnitzer et al. | |
| 5,715,812 A | 2/1998 | Deighan et al. | |
| 5,752,509 A | 5/1998 | Lachmann et al. | |
| 5,762,480 A | 6/1998 | Adahan | |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,881,717 A | 3/1999 | Isaza | |
| 5,881,723 A | 3/1999 | Wallace et al. | |
| 5,884,623 A | 3/1999 | Winter | |
| 5,891,023 A | 4/1999 | Lynn | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 6,024,089 A | 2/2000 | Wallace et al. | |
| 6,041,780 A | 3/2000 | Richard et al. | |
| 6,047,860 A | 4/2000 | Sanders | |
| 6,076,523 A | 6/2000 | Jones et al. | |
| 6,116,240 A | 9/2000 | Merrick et al. | |
| 6,116,464 A | 9/2000 | Sanders | |
| 6,123,073 A | 9/2000 | Schlawin et al. | |
| 6,123,074 A | 9/2000 | Hete et al. | |
| 6,135,106 A | 10/2000 | Dirks et al. | |
| 6,142,150 A | 11/2000 | O'Mahony et al. | |
| 6,148,814 A | 11/2000 | Clemmer et al. | |
| 6,158,432 A | 12/2000 | Biondi et al. | |
| 6,161,539 A | 12/2000 | Winter | |
| 6,220,245 B1 | 4/2001 | Takabayashi et al. | |
| 6,223,064 B1 | 4/2001 | Lynn et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,342,039 B1 | 1/2002 | Lynn et al. | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,371,114 B1 | 4/2002 | Schmidt et al. | |
| 6,390,091 B1 | 5/2002 | Banner et al. | |
| 6,412,483 B1 | 7/2002 | Jones et al. | |
| 6,439,229 B1 | 8/2002 | Du et al. | |
| 6,467,478 B1 | 10/2002 | Merrick et al. | |
| 6,512,938 B2 | 1/2003 | Claure et al. | |
| 6,532,958 B1 | 3/2003 | Buan et al. | |
| 6,532,959 B1 | 3/2003 | Berthon-Jones | |
| 6,532,960 B1 | 3/2003 | Yurko | |
| 6,536,429 B1 | 3/2003 | Pavlov et al. | |
| 6,543,449 B1 | 4/2003 | Woodring et al. | |
| 6,546,930 B1 | 4/2003 | Emerson et al. | |
| 6,553,991 B1 | 4/2003 | Isaza | |
| 6,557,553 B1 | 5/2003 | Borrello | |
| 6,561,187 B2 | 5/2003 | Schmidt et al. | |
| 6,571,795 B2 | 6/2003 | Bourdon | |
| 6,609,016 B1 | 8/2003 | Lynn | |
| 6,622,726 B1 | 9/2003 | Du | |
| 6,640,806 B2 | 11/2003 | Yurko | |
| 6,644,310 B1 | 11/2003 | Delache et al. | |
| 6,644,312 B2 | 11/2003 | Berthon-Jones et al. | |
| 6,668,824 B1 | 12/2003 | Isaza et al. | |
| 6,671,529 B2 | 12/2003 | Claure et al. | |
| 6,675,801 B2 | 1/2004 | Wallace et al. | |
| 6,688,307 B2 | 2/2004 | Berthon-Jones | |
| 6,718,974 B1 | 4/2004 | Moberg | |
| 6,723,055 B2 | 4/2004 | Hoffman | |
| 6,725,447 B1 | 4/2004 | Gilman et al. | |
| 6,739,337 B2 | 5/2004 | Isaza | |
| 6,748,252 B2 | 6/2004 | Lynn et al. | |
| 6,752,151 B2 | 6/2004 | Hill | |
| 6,758,216 B1 | 7/2004 | Berthon-Jones et al. | |
| 6,760,608 B2 | 7/2004 | Lynn | |
| 6,761,165 B2 | 7/2004 | Strickland, Jr. | |

(56) References Cited

U.S. PATENT DOCUMENTS

| | | | |
|---|---|---|---|
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,814,074 B1 | 11/2004 | Nadjafizadeh et al. |
| 6,820,618 B2 | 11/2004 | Banner et al. |
| 6,837,242 B2 | 1/2005 | Younes |
| 6,866,040 B1 | 3/2005 | Bourdon |
| 6,868,346 B2 | 3/2005 | Larson et al. |
| 6,960,854 B2 | 11/2005 | Nadjafizadeh et al. |
| 7,008,380 B1 | 3/2006 | Rees et al. |
| 7,036,504 B2 | 5/2006 | Wallace et al. |
| 7,066,173 B2 | 6/2006 | Banner et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,089,937 B2 | 8/2006 | Berthon-Jones et al. |
| 7,092,757 B2 | 8/2006 | Larson et al. |
| 7,100,609 B2 | 9/2006 | Berthon-Jones et al. |
| 7,117,438 B2 | 10/2006 | Wallace et al. |
| 7,152,598 B2 | 12/2006 | Morris et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,460,959 B2 | 12/2008 | Jafari |
| 7,472,702 B2 | 1/2009 | Beck et al. |
| 7,487,773 B2 | 2/2009 | Li |
| 7,509,957 B2 | 3/2009 | Duquette et al. |
| 7,520,279 B2 | 4/2009 | Berthon-Jones |
| 7,527,054 B2 | 5/2009 | Misholi |
| 7,654,802 B2 | 2/2010 | Crawfor, Jr. et al. |
| 7,668,579 B2 | 2/2010 | Lynn |
| 7,694,677 B2 | 4/2010 | Tang |
| 7,717,113 B2 | 5/2010 | Andrieux |
| 7,758,503 B2 | 7/2010 | Lynn et al. |
| 7,784,461 B2 | 8/2010 | Figueiredo et al. |
| 7,802,571 B2 | 9/2010 | Tehrani |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,984,714 B2 | 7/2011 | Hausmann et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| 8,181,648 B2 | 5/2012 | Perine et al. |
| 8,210,173 B2 | 7/2012 | Vandine |
| 8,210,174 B2 | 7/2012 | Farbarik |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,551,006 B2 | 10/2013 | Karst et al. |
| 8,792,949 B2 | 7/2014 | Baker, Jr. |
| 2002/0185126 A1 | 12/2002 | Krebs |
| 2003/0158466 A1 | 8/2003 | Lynn et al. |
| 2003/0221689 A1 | 12/2003 | Berthon-Jones |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2006/0112959 A1 | 6/2006 | Mechlenburg et al. |
| 2006/0144144 A1 | 7/2006 | Seto |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0241708 A1 | 10/2006 | Boute |
| 2006/0264762 A1 | 11/2006 | Starr |
| 2006/0272642 A1 | 12/2006 | Chalvignac |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044805 A1 | 3/2007 | Wedler et al. |
| 2007/0072541 A1 | 3/2007 | Daniels, II et al. |
| 2007/0077200 A1 | 4/2007 | Baker |
| 2007/0093721 A1 | 4/2007 | Lynn et al. |
| 2007/0129647 A1* | 6/2007 | Lynn ................... A61B 5/00 600/538 |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0227537 A1 | 10/2007 | Bemister et al. |
| 2007/0272241 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0000479 A1 | 1/2008 | Elaz et al. |
| 2008/0044505 A1* | 2/2008 | Bae et al. ................. 424/776 |
| 2008/0045845 A1* | 2/2008 | Pfeiffer et al. ............ 600/485 |
| 2008/0053441 A1 | 3/2008 | Gottlib et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0178880 A1 | 7/2008 | Christopher et al. |
| 2008/0178882 A1 | 7/2008 | Christopher et al. |
| 2008/0200775 A1 | 8/2008 | Lynn |
| 2008/0200819 A1 | 8/2008 | Lynn et al. |
| 2008/0236582 A1 | 10/2008 | Tehrani |
| 2008/0251079 A1 | 10/2008 | Richey |
| 2008/0314385 A1 | 12/2008 | Brunner et al. |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0326389 A1* | 12/2009 | Ralfs ......................... 600/485 |
| 2010/0006098 A1 | 1/2010 | McGinnis et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |

(56) References Cited

U.S. PATENT DOCUMENTS

| | | |
|---|---|---|
| 2010/0071689 A1 | 3/2010 | Thiessen |
| 2010/0071695 A1 | 3/2010 | Thiessen |
| 2010/0071696 A1 | 3/2010 | Jafari |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186742 A1 | 7/2010 | Sherman et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2010/0331639 A1 | 12/2010 | O'Reilly |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0259330 A1 | 10/2011 | Jafari et al. |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
U.S. Appl. No. 12/561,960, Notice of Allowance mailed Jun. 4, 2012, 12 pgs.
U.S. Appl. No. 12/561,960, Notice of Allowance mailed Jun. 7, 2013, 9 pgs.
U.S. Appl. No. 12/561,960, Notice of Allowance mailed Aug. 8, 2012, 8 pgs.

* cited by examiner

METHOD FOR DETERMINING HEMODYNAMIC EFFECTS

RELATED APPLICATIONS

This application is a continuation application of and claims the benefit of priority from U.S. patent application Ser. No. 12/561,960, filed on Sep. 17, 2009, now issued U.S. Pat. No. 8,551,006 which claims priority to U.S. Patent Application Ser. No. 61/097,763, filed on Sep. 17, 2008, the entire disclosures of which are hereby incorporated herein by reference.

FIELD OF THE DISCLOSURE

The present disclosure relates, in some embodiments, to devices, systems, and/or methods for collecting, processing, and/or displaying stroke volume and/or cardiac output data.

BACKGROUND OF THE DISCLOSURE

Most oxygen delivered to tissue is carried by hemoglobin. The proportion of oxygen delivered by hemoglobin may drop somewhat for a patient breathing very high levels of oxygen, however. A pulse oximeter may use the time-varying optical response of different wavelengths of light traveling through tissue to estimate pulse rate and the fraction of hemoglobin that carries oxygen molecules in the pulsatile portion. Each data point in the pulse oximeter's time series of optical response measurements represents the quantity of those photons of light that travel on a path from light emitter to light detector and are successfully measured by the detector. The signal level may be reduced by, for example, optical attenuation and scattering of tissue along the path from emitter to detector.

A pulse oximeter may measure changes in the amount of hemoglobin in a local area, along with the spectral response of the changes, over a cardiac cycle, without the need for an absolute reference. A photoplethysmogram (PPG) is an inverted, bandpass filtered graph of the optical response at one wavelength or a combination of wavelengths with respect to time. The ratio of pulse-synchronous change in absorption (PPG modulation) to average signal level is sometimes referred to as percent modulation, although this number depends on the relative quantities of different types of hemoglobin and other absorbers.

An optical sensor may be positioned at a tissue site on a subject that includes a concentration of smaller blood vessels. The light transmitted through these smaller blood vessels may decrease during the pressure wave of systole because of an attending greater volume of absorbers in the distended vessels of the vascular tree. The optical signal may rebound (e.g., increase) during diastole when lower pressure allows the amount of absorbers to decrease. Although the flow of fresh blood may take many seconds to travel to a peripheral site, the pressure waveform traverses the pressurized arterial tree within a much shorter time span. Vascular resistance and compliance of the small arteries, arterioles and capillaries reduces pressure and largely damps out any pulse-synchronous volume changes distal to these vessels.

Empirical calibrations of pulse oximeters using blood-gas measurements may include one or more assumptions that impact accuracy. For example, while tissue sites where pulse oximeters may be used may include arteries and arterioles as the primary conduit for delivering oxygen-rich blood from the left heart to tissue, these tissue sites generally comprise several other tissues and/or structures.

A number of factors may affect average optical response and pulse-synchronous modulation, particularly at peripheral sensor sites such as the finger, ear or foot. The body's control of circulation to the periphery is particularly used for temperature regulation, with vasodilation increasing peripheral blood flow to disperse heat and vasoconstriction acting to minimize the body's loss of heat. Local blood perfusion adapts based on tissue needs and metabolic activity. Drugs, therapies and shifts in fluid or electrolyte content may lead to changes in the distribution of systemic blood flow to the various organs, including the skin. This may also lead to changes in optical response and modulation. Shock, trauma or infection may cause adjustments in blood distribution. Changes in cerebral, muscular, renal or splanchnic circulation, hormonal activity and disease states also may have a significant influence on peripheral blood flow.

These factors may make it difficult to estimate the heart's total stroke volume based on the measurement of blood volume changes at a single sensor site. A "perfusion index" may be used on some occasions, but such a parameter may not adequately account for the myriad influences on distribution of blood flow to different parts of the body. Thus, a perfusion index at a peripheral sensor location may not provide a direct indication of stroke volume and cardiac output, nor even the adequacy of tissue perfusion at the sensor site.

SUMMARY

Accordingly, a need has arisen for improved devices, systems, and methods for determining stroke volume and/or cardiac output of a subject.

The present disclosure relates, in some embodiments, to devices, systems, and/or methods for collecting, processing, and/or displaying stroke volume and/or cardiac output data. According to some embodiments, a device for assessing changes in cardiac output and/or stroke volume of a subject receiving airway support from a breathing assistance system may comprise a processor; an airway sensor in communication with the processor, wherein the airway sensor is configured and arranged to sense pressure in the subject's airway, lungs, and/or intrapleural space over time; a blood volume sensor in communication with the processor, wherein the blood volume sensor is configured and arranged to sense pulsatile volume of blood in a tissue of the subject over time; and a display configured and arranged to display a representative of an airway pressure, a pulsatile blood volume, a photoplethysmogram, a photoplethysmogram ratio, the determined cardiac output and/or stroke volume, or combinations thereof. A processor of a device may be configured and arranged, in some embodiments, to (a) produce a photoplethysmogram, (b) determine a photoplethysmogram ratio of the amplitude of the photoplethysmogram during inhalation to the amplitude of the photoplethysmogram during exhalation, and (c) determine the change in cardiac output and/or stroke volume of the subject using the ratio of the amplitude of the photoplethysmogram during inhalation to the amplitude of the photoplethysmogram during exhalation.

In some embodiments, a device for assessing changes in cardiac output or stroke volume of a subject receiving airway support from a breathing assistance system may comprise an airway sensor configured and arranged to sense pressure in the subject's airway, lungs, and/or intrapleural space over time; a blood volume sensor configured and arranged to sense pulsatile volume of blood in a tissue of the subject over time; a processor configured and arranged (a) to receive input from the airway sensor and the blood volume sensor, (b) to produce a photoplethysmogram; (c) to determine a photoplethysmogram ratio of the amplitude of the photoplethysmogram during inhalation to the amplitude of the photoplethysmogram during exhalation, and (d) to determine the change in cardiac output and/or stroke volume of the subject using the determined ratio; and a display configured and arranged to display a representative of a parameter selected from the group consisting of the sensed airway pressure, the sensed pulsatile blood volume, the photoplethysmogram, the determined ratio, the determined cardiac output and/or stroke volume, combinations thereof. The airway sensor of a device for assessing changes in cardiac output or stroke volume of a subject, according to some embodiments, may be configured and arranged to sense pressure in the subject's airway intermittently and/or continuously. The blood volume sensor of a device for assessing changes in cardiac output or stroke volume of a subject may be configured and arranged to sense pulsatile volume of blood in a tissue of the subject intermittently and/or continuously in some embodiments. The blood volume sensor of a device for assessing changes in cardiac output or stroke volume of a subject, according to some embodiments, may be comprised in a pulse oximeter. In some embodiments, the representative of a parameter may be the actual parameter value. The representative of a parameter may be a graphical representation of the actual parameter value according to some embodiments. The breathing assistance system of a device for assessing changes in cardiac output or stroke volume of a subject, in some embodiments, may be selected from the group consisting of a ventilator, a respirator, a CPAP device, a BiPAP device, and combinations thereof. According to some embodiments, a device for assessing changes in cardiac output or stroke volume of a subject may further comprise a pulse rate sensor in communication with the processor. The processor of a device for assessing changes in cardiac output or stroke volume of a subject may be configured and arranged to calculate cardiac output by multiplying the stroke volume by the pulse rate in some embodiments.

A system for assessing changes in cardiac output or stroke volume of a subject may comprise, according to some embodiments, (a) a breathing assistance system, (b) a pulse oximeter comprising a blood volume sensor, (c) a display system, and (d) a processor in communication with the breathing assistance system, the display system, and the pulse oximeter, wherein the processor is configured and arranged to (a) produce a photoplethysmogram, (b) determine the ratio of the amplitude of the photoplethysmogram during inhalation to the amplitude of the photoplethysmogram during exhalation, and (c) determine the change in cardiac output or stroke volume of the subject using the ratio of the amplitude of the photoplethysmogram during inhalation to the amplitude of the photoplethysmogram during exhalation. In some embodiments, (a) a breathing assistance system may comprise (1) a ventilation system, (2) an airway connection system configured and arranged to link the ventilation system and the subject's airway, and/or (3) an airway pressure sensor configured and arranged to detect pressure in the ventilation system and/or the subject's airway. The airway sensor of a system for assessing changes in cardiac output or stroke volume of a subject may be configured and arranged to sense pressure in the subject's airway (e.g., airway, lungs, and/or intrapleural space) intermittently and/or continuously according to some embodiments. The blood volume sensor of a system for assessing changes in cardiac output or stroke volume of a subject, in some embodiments, may be configured and arranged to sense pulsatile volume of blood in a tissue of the subject intermittently and/or continuously. According to some embodiments, the breathing assistance system of a system for assessing changes in cardiac output or stroke volume of a subject may be selected from the group consisting of a ventilator, a respirator, a CPAP device, a BiPAP device, and combinations thereof. The processor of a system for assessing changes in cardiac output or stroke volume of a subject may be configured and arranged to calculate cardiac output by multiplying the stroke volume by the pulse rate in some embodiments.

A method of assessing changes in cardiac output or stroke volume of a subject receiving airway support from a breathing assistance system, in some embodiments, may comprise sensing pressure in the subject's airway as a function of time, sensing pulsatile volume of blood in a tissue of the subject as a function of time, producing a photoplethysmogram from the sensed pulsatile volume, determining the ratio of the amplitude of the photoplethysmogram during inhalation to the amplitude of the photoplethysmogram during exhalation, and determining the change in cardiac output or stroke volume of the subject using the determined ratio. According to some embodiments, a method of assessing changes in cardiac output or stroke volume of a subject receiving airway support from a breathing assistance system may further comprise displaying a representative of the sensed pressure, the sensed pulsatile blood volume, the photoplethysmogram, the determined ratio, the determined cardiac output or stroke volume, or combinations thereof. A method of assessing changes in cardiac output or stroke volume of a subject receiving airway support from a breathing assistance system may further comprise sensing the subject's pulse in some embodiments. A method may further comprise, according to some embodiments, calculating the change in cardiac output by multiplying the change in cardiac output or stroke volume by the sensed pulse. In some embodiments, sensing pulsatile volume of blood in a tissue of the subject may comprise sensing pulsatile volume of blood in a subject's finger, ear, forehead or foot. A method of assessing changes in cardiac output or stroke volume of a subject receiving airway support from a breathing assistance system may further comprise referencing the stroke volume to a parameter selected from the group consisting of zero end-expiratory pressure, current active breathing assistance system control settings, and combinations thereof according to some embodiments.

According to some embodiments, a method of predicting the effect of changes in ventilation settings on stroke volume of a ventilated subject may comprise sensing pressure in the subject's airway during at least one breathing cycle comprising an inhalation and an exhalation, producing a photoplethysmogram spanning the at least one breathing cycle, determining the ratio of the amplitude of the photoplethysmogram during inhalation to the amplitude of the photoplethysmogram during exhalation, determining the change in cardiac output or stroke volume of the subject using the determined ratio, referencing the stroke volume to current active ventilation settings of the breathing assistance system, and combinations thereof, and comparing the change in changes in ventilation settings to the current active ventilation settings. The change in ventilation settings, in some embodiments, may comprise a change in a setting selected from the group consisting of positive end-expiratory pressure (PEEP), continuous positive airway pressure, inspiratory pressure target, inspiratory volume target, I:E ratio, and combinations thereof.

In some embodiments, a method of assessing the relative strength of an autonomic neural response of a subject connected to a breathing assistance system may comprise determining the cardiac output of the subject at a first airway pressure, changing the subject's airway pressure to a second airway pressure, monitoring the cardiac output of the subject at the second airway pressure, comparing the cardiac output of the subject at the second airway pressure with the cardiac output of the subject at the first airway pressure, measuring the time required for the cardiac output of the subject at the second airway pressure to return to the cardiac output of the subject at a first airway pressure, and comparing the required time to a reference time to determine the relative strength of an autonomic neural response of the subject.

BRIEF DESCRIPTION OF THE DRAWINGS

Some embodiments of the disclosure may be understood by referring, in part, to the present disclosure and the accompanying drawings, wherein.

DETAILED DESCRIPTION

For a subject (e.g., a patient) undergoing positive pressure ventilation or CPAP, a potential complication is the possibility of hemodynamic compromise. Depending on lung compliance and airway resistance, positive airway pressure exerted by a mechanical ventilator or a CPAP may device result in increased intrapleural pressure. There may exist a transfer function between airway pressure measured by a ventilator and intrapleural pressure exerted by the volume of gas in the lungs. A transfer function may vary (e.g., significantly) across a population and may change within an individual subject. To evaluate the effect of ventilation on hemodynamics, it may be desirable to sense (e.g., measure and/or estimate) pressure in the ventilator circuit, at the airway, in the lungs, and/or in the intrapleural space. The transmural pressure exerted on the vena cavae and other large veins, which may be at the lowest pressure of any part of the systemic circulation, may tend to inhibit venous return for some individuals. The immediate response to the resulting reduction in cardiac preload may be a lower stroke volume.

However, the intrapleural pressure also may act to reduce the effect of cardiac afterload, potentially adding to stroke volume. For individuals with high vascular volume and those with congestive heart failure (CHF), the increased intrapleural pressure may improve stroke volume by minimizing volume overload in the heart and great vessels. Balancing the need for respiratory support and hemodynamic stability often results in tradeoffs in clinical decision-making, such as adjustment of ventilator settings, fluid administration, and/or use of vasoactive drugs.

Figure 1:
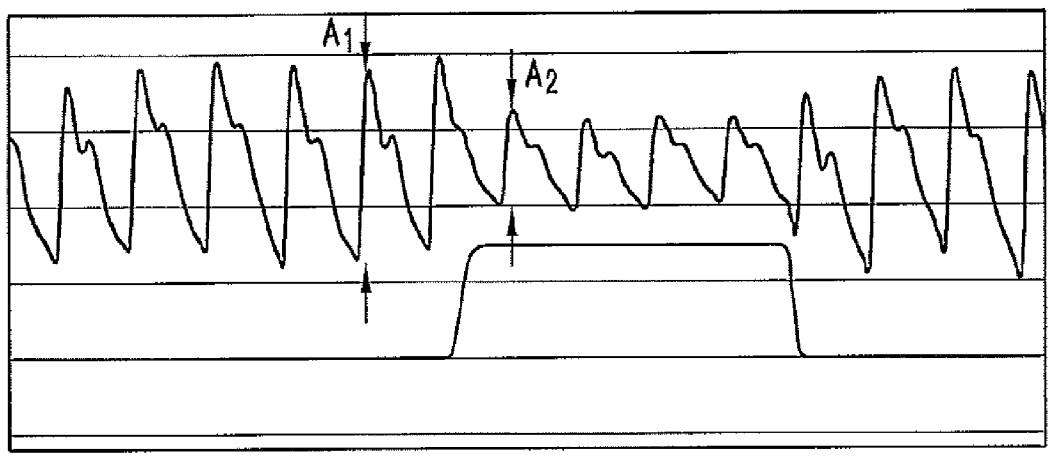
FIG. 1 illustrates a photoplethysmogram (top) and airway pressure (bottom) according to a specific example embodiment of the disclosure, wherein PPG amplitude is reduced during an inspiratory pressure plateau.

Because the respiratory cycle usually takes place over a matter of several seconds, it is both longer than the typical cardiac cycle and shorter than the time scale of shifts in blood distribution (e.g., the shifts described in the Background section). Resistances and elastances of the blood vessels may respond to the altered stroke volume over a course of time. Cardiovascular effects brought about by changes in thoracic pressure appear as modulation of the PPG waveform measured by a pulse oximetry sensor within the transit time of the pressure wave to the sensor site. Thus the breath-synchronous modulation of absorbers in the tissue probed by the pulse oximeter is a reflection of the short-term changes in stroke volume. In the simplest example of a pressure-targeted breath, as shown in FIG. 1, the envelope of the PPG waveform provides a direct indicator of the changes in stroke volume over the respiratory cycle. The amplitude ratio correlates with the stroke volume:

$$\frac{A_2}{A_1} \propto \frac{\text{Stroke volume during inspiration}}{\text{Stroke volume during exhalation}}$$

Expressed another way, the reduction in stroke volume during inspiration compared to a baseline stroke volume during exhalation is a function of the PPG modulation:

$$\frac{A_2}{A_1} - 1 \propto \Delta SV$$

Modulation of the PPG decreases during the inspiratory period, when there is a higher airway pressure plateau, and increases again to its previous level during exhalation.

The present disclosure relates to the use of the change in the PPG amplitude and/or or perfusion index to quantify the effect of airway pressure delivered by a positive pressure ventilator or CPAP device on stroke volume. Changes in cardiac output may be calculated from the product of stroke volume and heart rate (e.g., instantaneous heart rate). For individuals with pressure-targeted modes of ventilation, there may be two distinct pressure levels at which the relative cardiac output may be measured (e.g., the inspired pressure target (PIP) and exhalation pressure target (PEEP)). Calculations over multiple breaths provide increasing accuracy of the computations. For bi-level ventilation, there may be likewise multiple stable pressure plateaus (e.g., high and low PEEP settings). If an ascending (e.g., slowly ascending) ramp in pressure (i.e., the time for the ventilator to reach the inspired pressure target is longer than one or two pulse periods) is used to deliver gas to the patient, these intermediate pressures may also be used to detect relative changes in cardiac output, and/or pressure thresholds at which they occur, by analyzing the relationship of the pulse-to-pulse PPG amplitude with a time-synchronous measurement or estimate of airway, lung, or intrapleural pressure. While a gradual ascending pressure ramp may be explicitly set in pressure-target ventilation, similar ramps in pressure will typically occur in volume-targeted and spontaneous breathing modes (e.g., pressure support and proportional assist ventilation). When the relationship between a gradually ramping airway pressure and the PPG amplitude is being evaluated, it may be desirable to adjust the airway pressure for the pressure drop due to the resistance and/or compliance of the airway, endotracheal tube, and lungs, for example, where these factors may create significant time delays in transferring changes in airway pressure to the lungs. Some methods for assessing these aspects of respiratory mechanics are known to those skilled in the art of mechanical ventilation.

The ventilator or CPAP may also deliver deliberate modulations in airway pressure at moments of minimal airflow or spontaneous respiratory effort as a means of calculating the relative change in cardiac output. Such maneuvers include delivering breaths of known or above-target inspiratory pressure, delivering an exhalation pressure above the PEEP setting, and delivering brief end-inspiratory pauses prior to permitting exhalation.

The technique may include referencing some or all modulations in stroke volume and cardiac output to a baseline measurement at zero end-expiratory pressure (ZEEP) (e.g., atmospheric pressure), at a nominally low PEEP level (i.e., under 5 cm $H_2O$), and/or to the current active ventilator settings. The dependence of stroke volume or cardiac output on airway pressure may be plotted as a graph showing the percent reduction, or increase, compared to a measured or extrapolated reference level such as ZEEP.

Using the established relationship between airway pressure and cardiac output, the ventilator may be configured and arranged to predict the change in cardiac output arising from any adjustment in ventilator settings. Predicted hemodynamic effects of settings may be based on interpolated values or extrapolated from the shape of the relationship between airway pressure and cardiac output. For example, if the operator desired to increase PEEP, the ventilator may interpolate (e.g., via a processor) the change in cardiac output at the desired PEEP setting and the overall change in cardiac output across the respiratory cycle. For patients with CHF or volume overload, this technique may be especially useful, for example, where the ventilator displays the amount of PEEP that should be added to optimize cardiac output. Other ventilatory parameters that may be adjusted to improve cardiac output include, without limitation, ratio of inspiratory to expiratory time (I:E ratio), peak inspiratory pressure, volume delivered, and percent support, depending on the ventilatory mode.

A reduced envelope of the PPG at the inspiratory pressure plateau may not occur for all individuals. For example, if external pressure reduces cardiac output, a subject's autonomic nervous system may attempt to compensate by increasing ventricular inotropy and/or heart rate. This compensation (or lack thereof) may serve as an indicator of the degree to which mechanical ventilation compromises hemodynamic stability. For example, hemodynamic stability may not be compromised in a subject who experiences rapid and complete compensation for pressure-induced stroke volume modulation. Individuals with reduced autonomic response, on the other hand, may display a sharp change in PPG envelope at the beginning of the inspiratory pressure plateau, followed by a gradual return to the previous amplitude as the balance of sympathetic and parasympathetic effects adjusts. In some embodiments, this indicator may also correlate with depth of sedation, or with level of neural or medullary center activity.

According to some embodiments, the present disclosure relates to devices, systems, and methods for (1) detecting the vitality and sensitivity of the autonomic response, (2) detecting the depth of sedation, and/or (3) detecting neural and/or medullary center activity, comprising detecting a time-varying response of the PPG waveform to a pressure change and determining whether the response exceeds a preselected threshold.

According to some embodiments, the present disclosure relates to devices, methods, and/or systems for measuring modulation of stroke volume and cardiac output as a function of airway pressure provided by a breathing assistance system. For example, methods for assessing changes in stroke volume and/or cardiac output in a subject receiving respiratory support (e.g., with a ventilator and/or CPAP device), may include (a) detecting the subject's airway pressure, (b) detecting a photoplethysmogram signal having an amplitude, and (c) processing the airway pressure and the detected photoplethysmogram signal to produce a relative indication of changes in stroke volume and/or cardiac output of the subject. According to some embodiments, a photoplethysmogram signal may be detected with a pulse oximeter. Computing the indication of stroke volume and/or cardiac output may include processing the airway pressure to detect a respiratory cycle consisting of an inhalation and an exhalation. Computing the indication of stroke volume and/or cardiac output may include producing a PPG and determining the ratio of the PPG amplitude during an inspiration to the PPG amplitude during exhalation.

A breathing assistance system may be configured to provide breathing assistance (e.g., providing ventilation and/or treating an apnea or other breathing condition) to a subject (e.g., a patient). A breathing assistance system may include a ventilation system, a connection system for linking the breathing assistance system to at least a portions subject's airway, and optionally a display system and/or a display connection port. A display connection port may be configured and arranged to communicate (e.g., wired or wirelessly) with a display (e.g., a touch screen, an LCD, a projector, and/or a printer).

A ventilation system may comprise any device, apparatus, and/or system for delivering breathing gas to a patient. For example, a ventilation system may include a ventilator, a respirator, a CPAP device, or a BiPAP device. A ventilation system may include a gas delivery system, a control system, and one or more sensors. In addition, in some embodiments, a ventilation system may include a display system, while in other embodiments, a display system may be distinct form the ventilation system.

A connection system may be configured to deliver gas from a ventilation system to a subject (e.g., a patient) and/or to remove exhaust gas away from the subject. For example, a connection system may comprise any suitable type of breathing circuit (e.g., a single-limb or dual-limb circuit) and/or a patient connection apparatus. The patient connection apparatus may include any device or devices configured to connect the breathing circuit to one or more breathing passageways of the subject. For example, the patient connection apparatus may include a patient connection tube directly connected to the subject's trachea, an artificial airway (e.g., an endotracheal tube or other device) inserted in the subject's trachea, and/or a mask, cushion or nasal pillows positioned over the subject's nose and/or mouth. In embodiments including a patient connection tube, the patient connection tube may include a Wye (or "Y") connector.

A display may be operable to display various data regarding a subject, the operation of a ventilation system, the ventilation of a subject, and/or any other relevant data. A display system may be fully or partially integrated with a ventilation system. In some embodiments, a display system may be part of or otherwise associated with, a graphic user interface, which may be configured to display various information and/or provide an interface (e.g., a touch screen) for accepting input from human operators (e.g., to set or modify ventilation settings, to access data, to change or configure the display, to select and/or modify 3-D waveform representations, etc.). A display device may comprise any type of printer, screen or other visual display for displaying information regarding the patient's breathing patterns and/or the operation of a breathing assistance system. Information displayed may include actual data and/or representations thereof.

A device (e.g., a breathing assistance system, a display system, and/or a device for determining stroke volume and/or cardiac output) may include, according to some embodiments, a processor. A processor may include any system or device for executing code or logic instructions (e.g., software or firmware) for controlling display device, such as a microcontroller, a digital signal processor (DSP), an application specific integrated controller (ASIC), electrically-programmable read-only memory (EPROM), or a field-programmable gate array (FPGA), for example.

The present disclosure, according to some embodiments, relates to devices, methods, and/or systems for predicting the effect of proposed changes in ventilation settings (e.g., positive end-expiratory pressure (PEEP) and/or CPAP, inspiratory pressure target or I:E ratio (i.e., the ratio of total inspiration time to total exhalation time in a single ventilation cycle)) on stroke volume and/or cardiac output, wherein the proposed changes would alter mean intrapleural pressure. For example, methods for predicting the effect of a ventilator setting change on stroke volume and/or cardiac output may include (a) sensing pressure in the subject's airway, lung, or intrapleural space during at least one breathing cycle comprising an inhalation and an exhalation, (b) producing a photoplethysmogram spanning the at least one breathing cycle, (c) determining the ratio of the amplitude of the photoplethysmogram during inhalation to the amplitude of the photoplethysmogram during exhalation (d) determining the relative change in cardiac output and/or stroke volume of the subject using the determined ratio, (e) referencing the stroke volume to current active ventilation settings of the breathing assistance system, and combinations thereof, and (f) comparing the proposed changes in ventilation settings to the current active ventilation settings.

In some embodiments, the disclosure relates to devices, methods, and/or systems for evaluating the strength of an autonomic neural response based on timing of cardiovascular changes in reaction to ventilatory artifact. For example, a method of assessing the relative strength of an autonomic neural response of a subject connected to a breathing assistance system may comprise (a) determining an indication of the cardiac output and/or stroke volume of the subject at a first airway pressure, (b) changing the subject's airway pressure to a second airway pressure, (c) monitoring the indication of the cardiac output and/or stroke volume of the subject at the second airway pressure, (d) comparing the indication of cardiac output or stroke volume of the subject at the second airway pressure with the cardiac output and/or stroke volume of the subject at the first airway pressure, (e) measuring the time required for the indication of cardiac output and/or stroke volume of the subject at the second airway pressure to return to the level of cardiac output and/or stroke volume of the subject at the first airway pressure, and (f) comparing the required time to a reference time to determine the relative strength of an autonomic neural response of the subject.

As will be understood by those skilled in the art who have the benefit of the instant disclosure, other equivalent or alternative compositions, devices, methods, and systems for determining cardiac output and/or stroke volume can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of airway and blood plethysmographic sensors may be varied. In addition, the size of a device and/or system may be scaled up (e.g., to be used for adult subjects) or down (e.g., to be used for neonatal subjects) to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. All or a portion of a device and/or system for determining relative changes in cardiac output and/or stroke volume may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1

Figure 2:
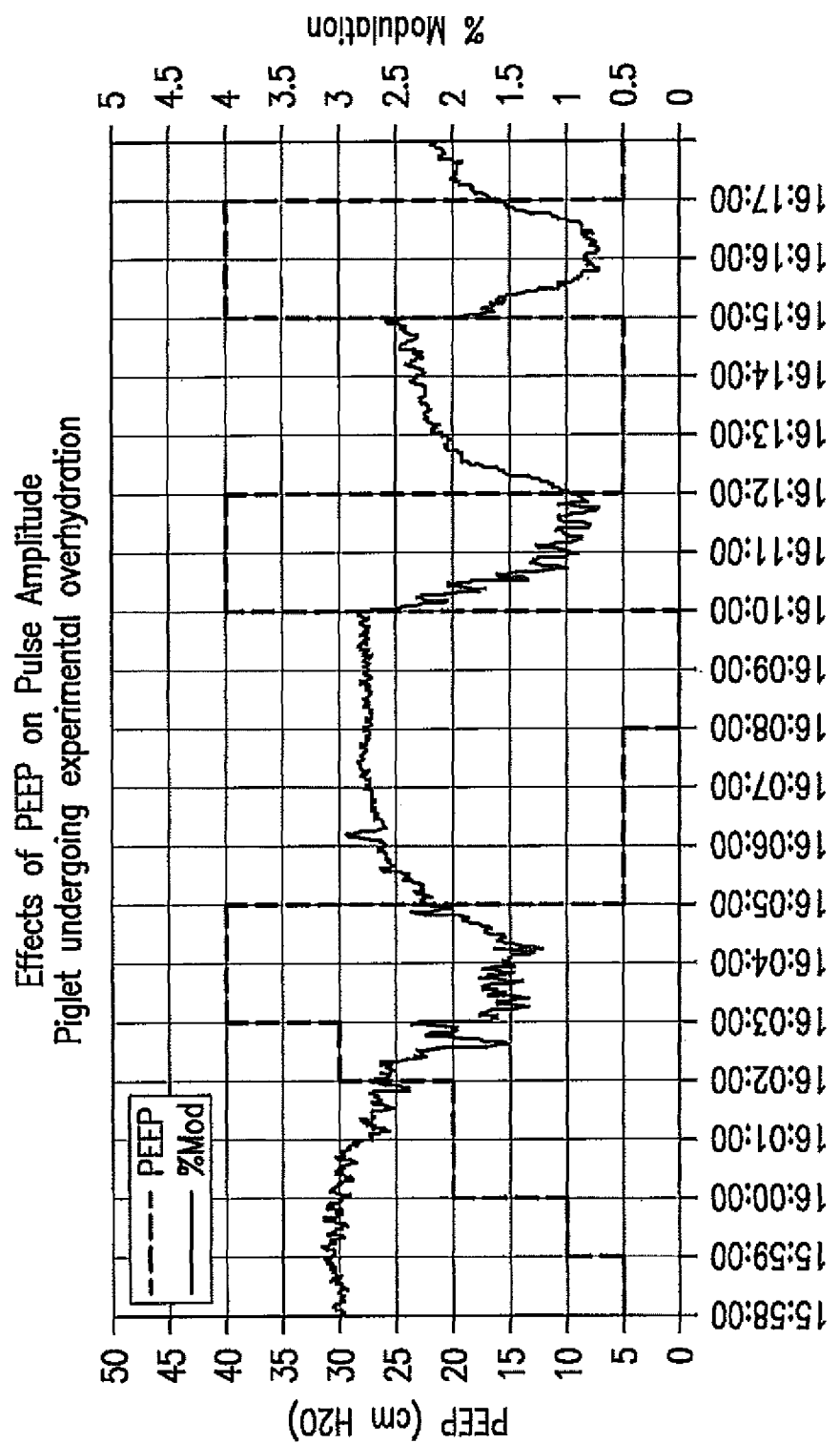
FIG. 2 illustrates changes in percent modulation (measured by a NELLCOR N-600 pulse oximeter) as a function of PEEP in an experimental animal model (e.g., an anesthetized piglet with healthy lungs undergoing fluid volume expansion by 30% of body weight).

In a ventilated animal subject, PEEP was gradually increased over five minutes from 5 to 40 cm $H_2O$ and a roughly 50% decrease in PPG modulation (from 3.0% to 1.5%) was observed (FIG. 2). In addition, a 65-70% decrease in PPG modulation (from 2.7% to % 0.9 and subsequently 2.4% to 0.8%) each of the two times that PEEP was increased in a single step from zero to 40 cm $H_2O$ (FIG. 2). Thus, modest reductions in PPG modulation occurred at 16:02:00 with when PEEP was increased from 20 to 30 cm $H_2O$, with very pronounced reductions in PPG amplitude for each of the periods when PEEP was increased to 40 cm $H_2O$.

This example indicates that that this particular animal subject experienced roughly 50% and later 65-70% reductions in stroke volume at a result of experiencing an airway pressure at or above 40 cm $H_2O$. Without necessarily limiting any particular embodiment to any specific mechanism of action, the smaller relative reduction in PPG modulation when PEEP was increased gradually may be due to difference in autonomic response.

What is claimed is:

1. A method of assessing changes in stroke volume or cardiac output of a ventilated subject, the method comprising:
    sensing pressure in the ventilated subject's airway during at least one breathing cycle comprising an inhalation and an exhalation with an airway sensor;
    sensing a blood volume in the ventilated subject during the at least one breathing cycle with a blood volume sensor;
    producing a photoplethysmogram spanning the at least one breathing cycle using the blood volume sensed by the blood volume sensor;
    determining, with a breathing assistance system, a ratio of the amplitude of the photoplethysmogram during inhalation to the amplitude of the photoplethysmogram during exhalation; and
    determining, with the breathing assistance system, a change in cardiac output or stroke volume of the subject using the determined amplitude ratio.

2. The method of according to claim 1, further comprising:
    referencing a stroke volume to current active ventilation settings of the breathing assistance system; and
    comparing changes in ventilation settings to the current active ventilation settings.

3. The method of according to claim 2, further comprising:
    determining a change in ventilation settings based on the change in cardiac output or stroke volume, wherein the change in ventilation settings comprises a change in a setting selected from the group consisting of positive end-expiratory pressure (PEEP), continuous positive airway pressure, inspiratory pressure target, inspiratory volume target, I:E ratio, and combinations thereof.

4. The method of according to claim 2, further comprising: displaying at least one of a representative parameter of the sensed airway pressure, a sensed pulsatile blood volume, the produced photoplethysmogram, the determined photoplethysmogram amplitude ratio, the cardiac output, or the stroke volume, the determined change in the cardiac output, the stroke volume.

5. The method of according to claim 2, wherein a representative parameter is a graphical representation of an actual parameter value.

6. The method of according to claim 2, wherein a representative parameter is an actual parameter value.

7. The method of according to claim 2, further comprising: sensing a pulse rate of the subject.

8. The method of according to claim 7, further comprising: determining the stroke volume of the subject from the determined photoplethysmogram amplitude ratio; calculating a cardiac output by multiplying the stroke volume by the pulse rate.

9. The method of according to claim 2, further comprising: changing the current active ventilation settings based on the comparing of the changes in ventilation settings to the current active ventilation settings, wherein the current active ventilation settings include at least one of positive-end expiratory pressure (PEEP), ratio of inspiratory time to expiratory time (I:E ratio), peak inspiratory pressure, volume delivered, and percent support.

10. The method of according to claim 1, further comprising: determining the stroke volume of the subject from the determined photoplethysmogram amplitude ratio; referencing the stroke volume to a parameter selected from a group consisting of zero end-expiratory pressure, current active breathing assistance system control settings, and combinations thereof.

11. A method of assessing a relative strength of an autonomic neural response of a subject connected to a breathing assistance system, the method comprising:
determining a cardiac output of the subject at a first airway pressure;
changing the subject's airway pressure to a second airway pressure via the breathing assistance system;
monitoring the cardiac output of the subject at the second airway pressure;
comparing, with the breathing assistance system, the cardiac output of the subject at the second airway pressure with the cardiac output of the subject at the first airway pressure;
measuring a time required for the cardiac output of the subject at the second airway pressure to return to the cardiac output of the subject at a first airway pressure;
comparing, with the breathing assistance system, the required time to a reference time; and
determining, with the breathing assistance system, the relative strength of an autonomic neural response of the subject using the comparing of the required time to the reference time.

12. The method of according to claim 11, further comprising: displaying at least one of a representative parameter of a sensed airway pressure, a pulsatile blood volume, a cardiac output and a stroke volume.

13. The method of according to claim 11, further comprising: displaying at least one of the required time and the reference time.

14. The method of according to claim 11, further comprising: displaying the determined relative strength of the autonomic neural response of the subject.

15. A processor comprising memory and a device, wherein the memory stores logic instructions and the device-executes the logic instructions stored on the memory, the logic instructions comprising:
instructions to produce a photoplethysmogram spanning at least one breathing cycle using processed sensor input;
instructions to determine a ratio of an amplitude of the photoplethysmogram during inhalation to an amplitude of the photoplethysmogram during exhalation; and
instructions to determine a change in cardiac output or stroke volume of a subject using the determined ratio.

16. The processor of claim 15, wherein the logic instructions further comprise:
instructions to monitor pressure in the subject's airway during at least one breathing cycle comprising an inhalation and an exhalation; and
instruction to monitor pulsatile volume of blood in a tissue of the subject as a function of time.

17. The processor of claim 15, wherein the logic instructions further comprise:
instructions to determine the stroke volume of the subject from the determined photoplethysmogram amplitude ratio;
instructions to calculate a cardiac output by multiplying the stroke volume by the pulse rate; and
instructions to display at least one of a representative parameter of an airway pressure, a pulsatile blood volume, the produced photoplethysmogram, the determined photoplethysmogram amplitude ratio, the cardiac output, the stroke volume, or the determined change in the cardiac output.

18. The method of according to claim 17, wherein the representative parameter is a graphical representation of an actual parameter value.

19. The method of according to claim 15, wherein the logic instructions further comprise:
instructions to sense a pulse rate of the subject.

20. The method of according to claim 19, wherein the logic instructions further comprise:
instructions to calculate a cardiac output by multiplying a stroke volume by the pulse rate.

* * * * *